United States Patent

Le Her

Patent Number: 5,832,094
Date of Patent: Nov. 3, 1998

[54] DEVICE FOR TRANSMISSION OF SOUND WITH SELECTIVE FILTERING FOR INSERTION IN THE OUTER AUDITORY CANAL

[76] Inventor: Francois Le Her, 330 rue Pasteur, Franqueville St Pierre—76520 Boos, France

[21] Appl. No.: 221,918

[22] Filed: Apr. 1, 1994

Related U.S. Application Data

[63] Continuation of Ser. No. 776,229, Nov. 12, 1991, abandoned.

[30] Foreign Application Priority Data

Feb. 1, 1990 [FR] France .................................. 90 01319
Feb. 1, 1991 [WO] WIPO ..................... PCT/FR91/00070

[51] Int. Cl.$^6$ .................................................. H04R 25/00
[52] U.S. Cl. ........................... 381/68.6; 381/69; 181/130
[58] Field of Search ........................... 381/68.6, 68, 68.2, 381/68.4, 69, 69.2, 159, 154; 181/129, 130, 135

[56] References Cited

U.S. PATENT DOCUMENTS

| | | |
|---|---|---|
| 2,619,960 | 12/1952 | Reynolds . |
| 2,785,675 | 3/1957 | Berkman . |
| 2,888,921 | 6/1959 | Nielson et al. . |
| 3,729,598 | 4/1973 | Tegt et al. ................................ 381/58 |
| 4,055,233 | 10/1977 | Huntress ................................ 381/187 |
| 4,311,206 | 1/1982 | Johnson ................................. 181/135 |
| 4,372,904 | 2/1983 | Gunn . |
| 4,442,917 | 4/1984 | Johnson ................................. 181/130 |
| 4,629,833 | 12/1986 | Kern et al. ............................. 381/68.2 |
| 4,811,402 | 3/1989 | Ward ...................................... 381/158 |
| 4,974,606 | 12/1990 | Van Mierlo ............................ 181/130 |
| 4,975,967 | 12/1990 | Rasmussen ............................ 381/68.6 |

FOREIGN PATENT DOCUMENTS

| | | |
|---|---|---|
| 0112594 | 7/1984 | European Pat. Off. . |
| 0197630 | 10/1986 | European Pat. Off. . |
| 2631815 | 5/1989 | European Pat. Off. . |
| 2108657 | 5/1972 | France . |
| 0916987 | 1/1988 | Germany . |
| 2197158 | 5/1988 | United Kingdom ................... 381/173 |

*Primary Examiner*—Huyen D. Le
*Attorney, Agent, or Firm*—Ostrolenk, Faber, Gerb & Soffen, LLP

[57] ABSTRACT

An earplug for selective filtering of sound transmission into the external auditory canal. A tube extends through the plug and opens into a space defined by the end piece and the eardrum of a user. The opposite end of the tube is connected to an acoustic valve which is partially or wholly inserted in the plug and contains one or more resonance cavities.

33 Claims, 4 Drawing Sheets

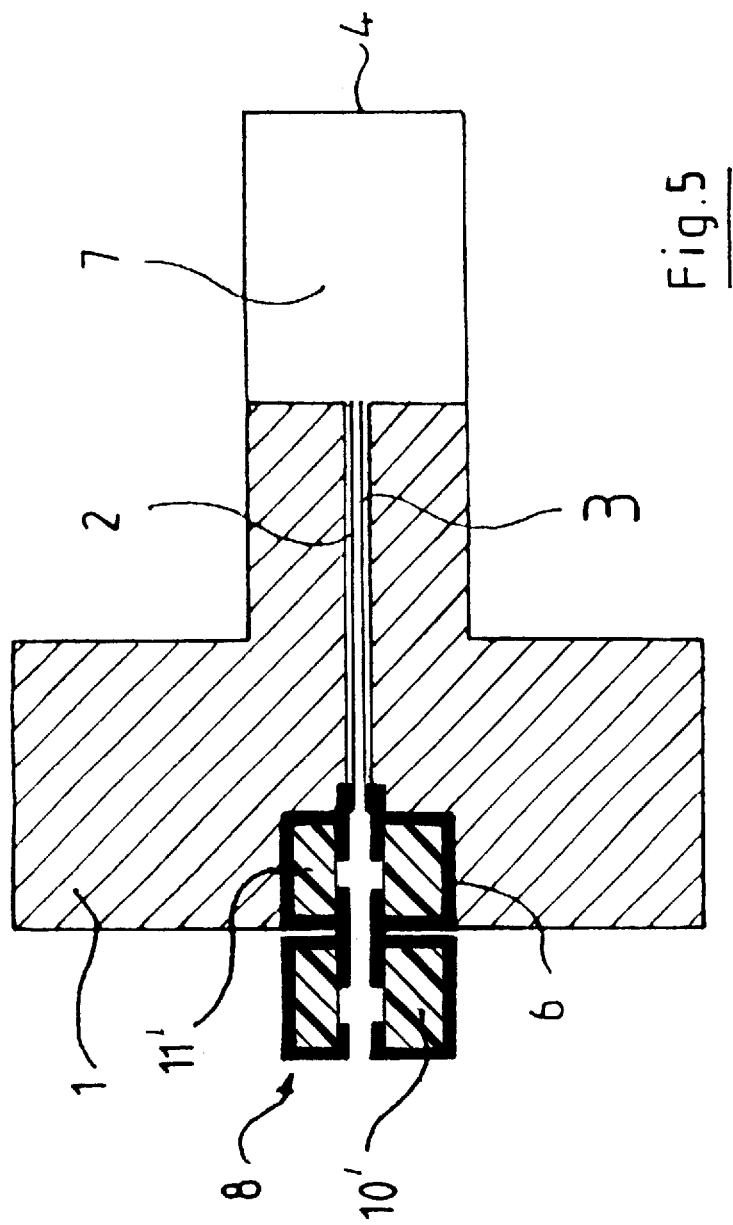

DEVICE FOR TRANSMISSION OF SOUND WITH SELECTIVE FILTERING FOR INSERTION IN THE OUTER AUDITORY CANAL

This is a Continuation of application Ser. No. 07/776,229 filed on Nov. 12, 1991, now abandoned.

BACKGROUND OF THE INVENTION

1. Field of the Invention

The present invention is directed to a device for transmission of sound with selective filtering for insertion in the outer auditory canal.

2. Description of the Related Art

To date there are several devices intended to protect individuals from noise, such as anti-noise helmets and ear plugs.

Anti-noise helmets are generally quite efficient in acoustic protection. However, there is a problem concerning the mechanical and acoustic tolerance of such helmets. Their efficiency varies in direct proportion to the pressure exercised on the outer ear and there is also the phenomenon of autophony.

Ear plugs typically consist of balls of soft wax that are pressed before being inserted into the outer auditory canal. These types of ear plugs are disadvantageous because they are difficult to position correctly, giving rise to a random contact with the outer auditory canal, and create the risk of germ contamination.

In order to solve this problem a protective plug directly molded on the auditory canal has been proposed. This plug is the subject of French patent 2,108,657, which teaches a plug molded in the auditory canal in an extended state so as to provide a good fit of the plug in the auditory canal.

However, this type of plug, while advantageous because it produces a precise and anatomical contact with the outer auditory canal, still has the disadvantage of autophony and also certain hygienic problems due to the fact that the silicon product injected in the auditory canal is polymerized by the serous fluids that are present.

To reduce autophony in this type of plug, various attempts have been made to manufacture protective plugs with a hole drilled in the plug. However, the length and diameter of these holes, as well as the residual volume between the eardrum and the end of the plug, affect the acoustic attenuation. Moreover, the random nature of the holes leads to considerable modifications in the acoustic response obtained.

To solve this problem, EP-A-0 112 594 teaches acoustic valves with holes drilled therein, the holes having a certain diameter and length. The valves may include an absorbing element. Nonetheless, the acoustic filter thus obtained is a second-order type filter, the attenuation slope of which is only 15 decibels per octave.

SUMMARY OF THE INVENTION

It is an object of the present invention to avoid the disadvantages of existing systems by providing a made-to-measure, individually molded, hearing protective device adapted to the acoustic environment of the wearer.

Another object of the invention is to provide a sound transmission device with selective filtering in the form of a plug that completely blocks the outer auditory canal, the plug including an acoustic valve and an open tube associated with at least one resonance cavity of the valve. According to the well known HELMHOLTZ resonator principle, the acoustic filter thus obtained is a fourth order filter with an attenuation slope of 30 decibels per octave.

The plug for the device is made from a mold taken from the wearer's ear using the same techniques as those used in hearing aids. Thus, after being cut and prepared, the mold is soaked in a solution of hot wax. A countermold is then made in one or two parts. The plug material is then poured into the counter mold and baked under pressure so as to be perfectly polymerized. The plug is then removed from the counter mold and coated with varnish. Two consecutive varnishing operations cause the plug to be thicker than the mold. The effect of this is to prevent any acoustic leaks resulting from the fact that the sides of the outer auditory canal are slightly compressed when the device is put into place.

According to the invention, the plug is preferably made of an anallergic medical silicon, but it could also be polymethylmethacrylate polymerized at high pressure and high temperature.

To make the plug, a tubular cavity is drilled, and a tube is placed in the tubular cavity. The tube extends through the plug and out into a residual cavity between the plug and the eardrum. Next, an acoustic valve is inserted in a recess in the plug at the end of the tube. The acoustic valve contains a plurality of resonance cavities. Each resonance cavity may be empty or filled with an acoustic absorbing element, such as synthetic foam or cellulose wadding, depending on the degree of sound absorption sought.

Depending on the frequency of the sound vibrations to be absorbed, the diameter of the open tube may vary from 0.1 to 2.2 mm and have length from 10 to 25 mm, each resonance cavity having a volume varying from 0.1 to 3 $cm^3$.

In an acoustic valve containing more than one resonance cavity, the cavities may be located outside the plug or be completely or partially within the plug.

The device may be modified to enable the wearer to communicate with a correspondent. In this case, the acoustic valve contains a receiver in one of the resonance cavities. This receiver is linked to a radio transmitter-receiver by an appropriate connection device and is also linked by an electric wire to a microphone located in the cavity in the plug, a short distance from the residual cavity. The microphone is linked by a tube set in a drilled hole and captures sound waves which cross the eardrum when the wearer speaks. The wearer can then speak, without having to raise his voice, and give a message that is not interfered with by ambient noise and he can also receive a message back.

The device may be modified by replacing the microphone with another transducer which is both a microphone and a receiver. In this case, the receiver is removed, with the transducer being directly linked to the connection device which in turn is linked to the radio transmitter-receiver.

This invention will be better understood after reading the following description and studying the drawings. It should be clearly understood that this description does not limit the invention in any way.

BRIEF DESCRIPTION OF THE DRAWINGS

In the drawings:

FIG. 5 shows a modification of the embodiment of FIG. 2.

DETAILED DESCRIPTION OF THE PREFERRED EMBODIMENT

Figure 1:
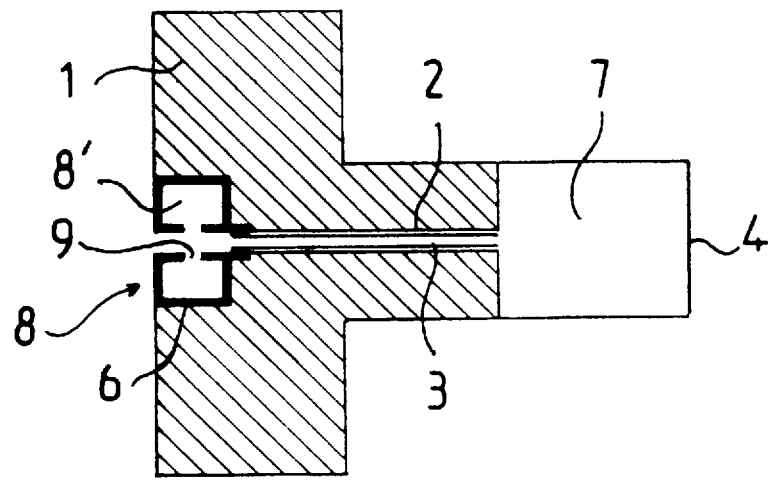
FIG. 1 shows a cross-sectional view of a device according to the invention.

Referring now to FIG. 1, the device according to the invention contains a plug 1 provided with a drill hole 2, within which is disposed a tube 3. Tube 3 extends through plug 1 to valve 8 inserted in a housing 6 fitted in plug 1. Valve 8 includes at least one resonance cavity 8' with an opening 9. At its inner extremity, tube 3 opens out into a residual cavity 7 between the inner surface plug of the plug 1 and the eardrum 4.

It is easy to see that this system enables a whole range of acoustic filters of the 4th order to be put into place. This can be obtained by modifying the diameter of tube 3, the volume of the resonance cavity 8' of the valve 8 and the volume of the residual cavity 7 between the plug 1 and the eardrum 4. Such a filter provides an acoustic attenuation slope of 30 decibels per octave.

Figure 2:
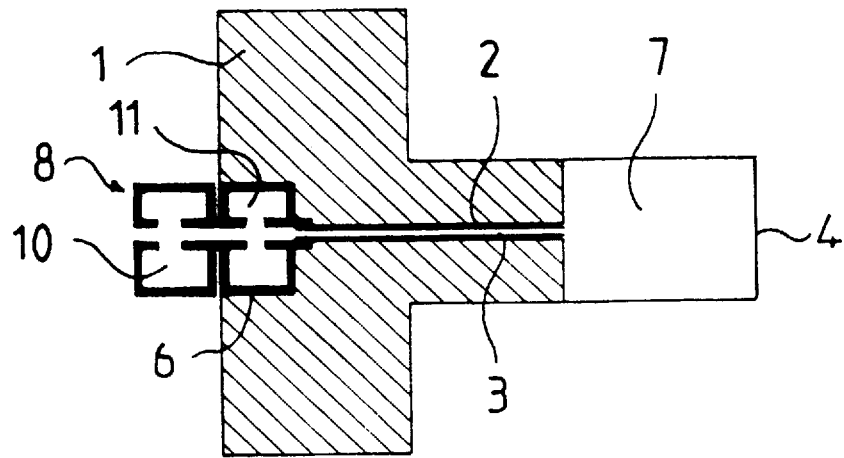
FIG. 2 shows a cross-sectional view of a second device according to the invention.

Referring now to FIG. 2, this device is a more absorbent filter than the preceding one. This is due to the fact that valve 8 is made up of two resonance cavities 10 and 11, the first of which is outside knob 1, whereas the second is inserted in it. The various parameters of this device, namely the length of tube 3, the volume of resonance cavities 10 and 11 of acoustic valve 8 and the volume of the residual cavity 7 between the plug 1 and the eardrum 4 also enable the acoustic filter to be modulated by adapting it to the sound context of the wearer.

FIG. 5 shows a device similar to that in FIG. 2, but in which the two resonance cavities 10' and 11' contain acoustically absorbent material.

Another variation of the device according to the invention is to have both acoustic valves in FIGS. 1 and 2 protected by a metal crown that can be sunk or clipped into plug 1 in order to accentuate low frequency attenuation in some special cases.

Figure 3:
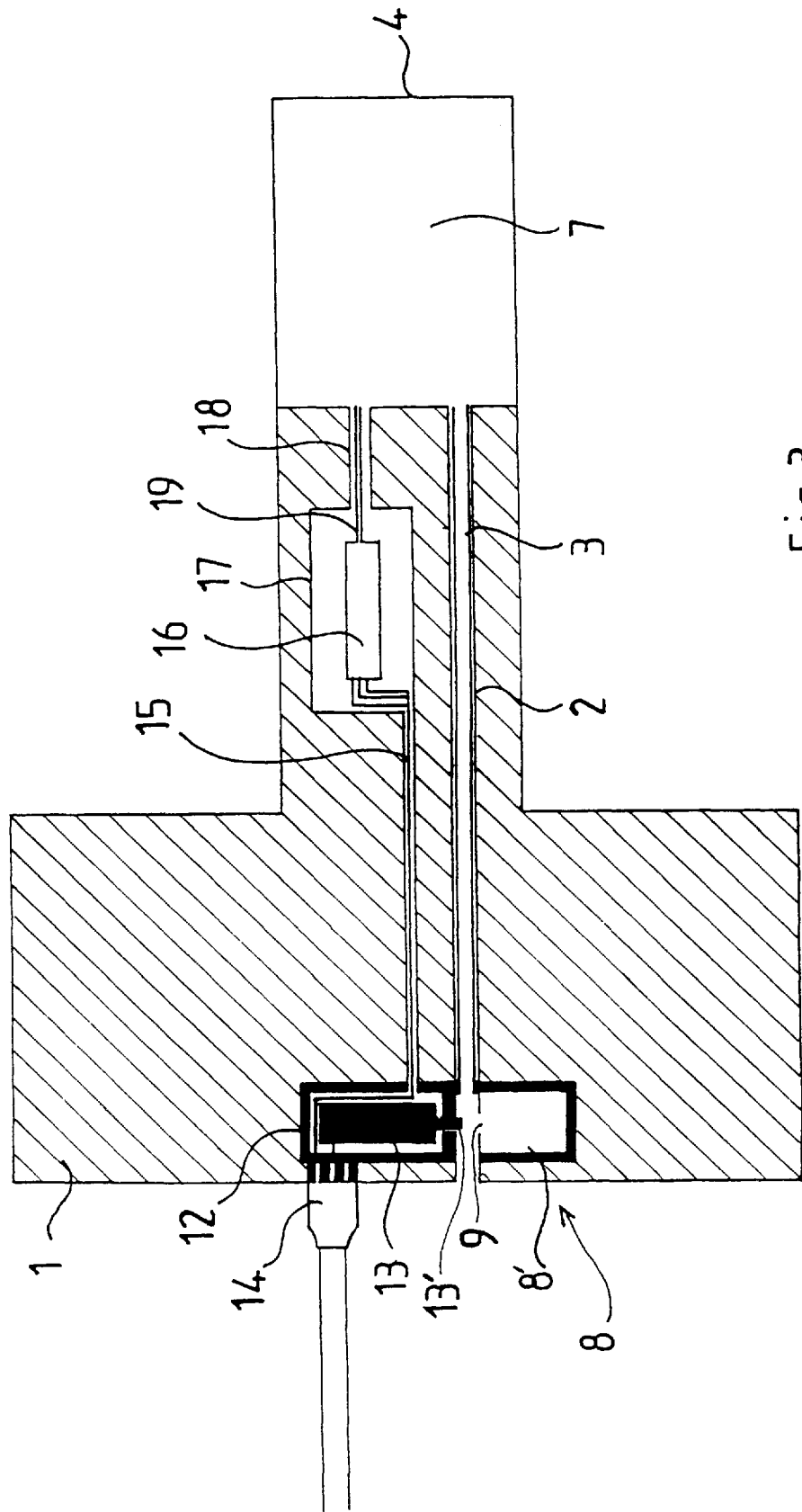
FIG. 3 shows a cross sectional view of a device according to the invention that is adapted to transmit the voice of the wearer to a high frequency radio communication system.

Referring now to FIG. 3, there is shown a device adapted for transmission of the voice of the wearer to an external radio transmitter-receiver (not shown), portable or not. In this case, the device contains a plug 1 with a drill hole 2 in which is placed a tube 3 extending through plug 1 to an acoustic valve 8 formed by a resonance cavity 8' in which is fitted a housing 12 for a receiver (earphone) 13. Outlet 13' of receiver 13 opens out onto the tube 3 and is linked to a connection device 14 linked to a transmitter-receiver. The connection device 14 is also linked, by electric wire 15, to a microphone 16 housed in the cavity 17. A tube 19 is attached to microphone 16 which captures sound waves which cross the eardrum when the wearer speaks.

A sufficiently sensitive microphone 16 with an adapted response curve enables sound waves of the voice of the wearer to be picked up in cavity 7 without picking up external sound waves that come through tube 3. This type of device is especially useful when the wearer and his correspondent are in particularly noisy environments such as those in which certain machine tools are continually activated, thus enabling them to communicate without the microphone picking up outside noises.

Figure 4:
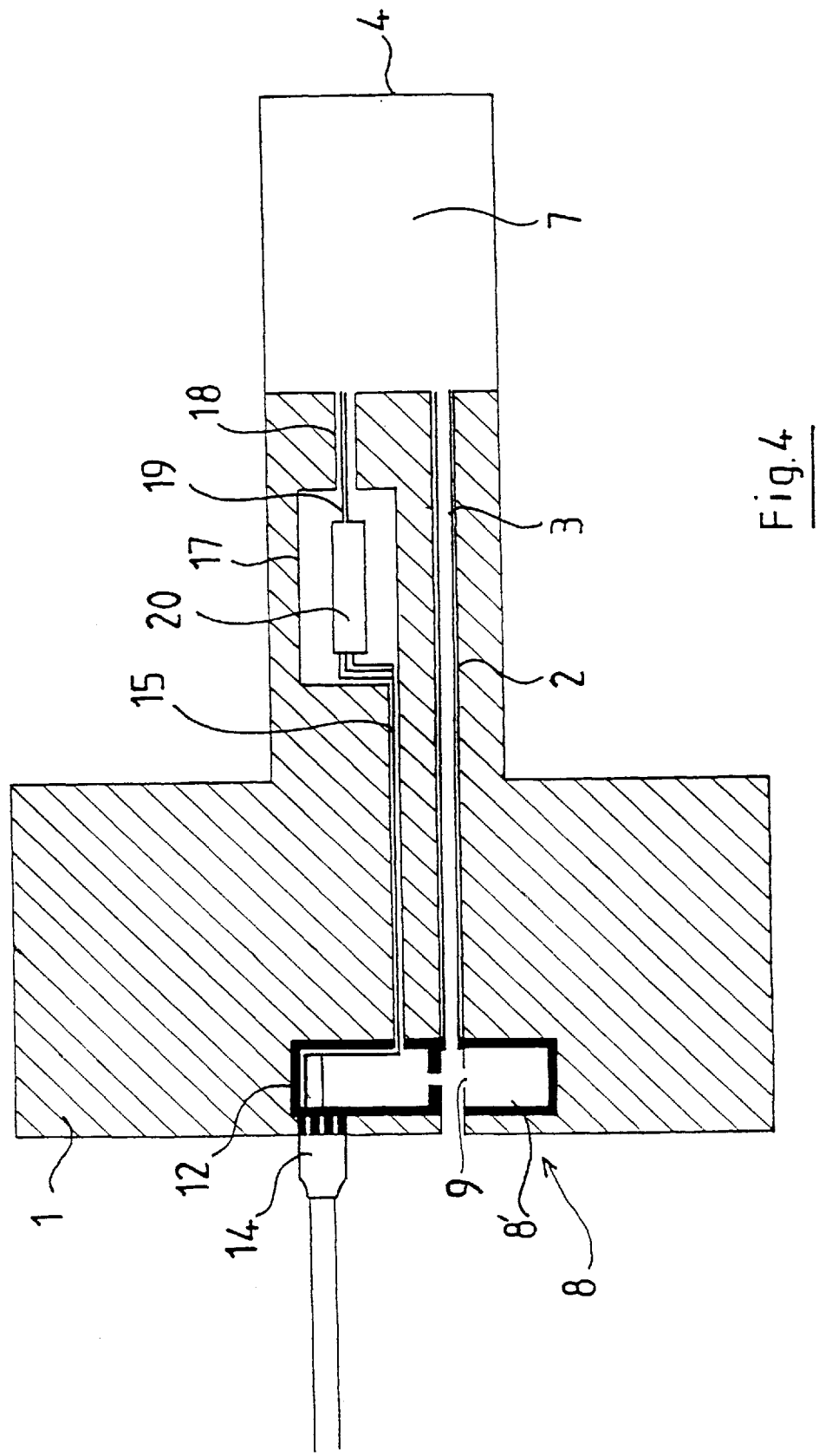
FIG. 4 shows a cross sectional view of an alternate embodiment according to the invention that is adapted to transmit the voice of the wearer to a high frequency radio communications system.

Referring now to FIG. 4, an alternate embodiment of the present invention is shown. Microphone 16 may be replaced by another transducer 20 which is both a microphone and a receiver. In this case, the receiver 13 is removed and the electric wire 15 directly links connector 14 to transducer 20.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

I claim:

1. Sound transmission device with selective filtration for being placed in the external auditory canal of a user, including a plug provided with a hole and an acoustic valve at least partially within said plug, said plug being fittable in the auditory canal of the user, the device comprising a tube which opens at its inner end into the residual cavity existing between the plug and the eardrum, and opening at its outer end into the acoustic valve, the acoustic valve defining at one resonance cavity, wherein said residual cavity and said acoustic valve are acoustically coupled by said tube so as to form a fourth-order acoustic filter.

2. The device of claim 1, further comprising acoustically absorbent material located within the resonance cavity.

3. The device of claim 1, wherein the acoustic valve comprises two resonance cavities, one of the resonance cavities being located outside the plug.

4. The device of claim 3, further comprising acoustically absorbent material located within both resonating cavities.

5. The device of claim 1, wherein the tube has a length of 10 to 25 mm and a diameter of 0.1 to 2.2 mm.

6. The device according to claim 5, wherein each resonance cavity has a volume of 0.1–3 cubic centimeters.

7. The device of claim 1, wherein the plug is formed of high-temperature interlaced silicon.

8. The device of claim 1, wherein the plug is formed of a polymethylmethacrylate which is completely polymerizable by heating under pressure before molding.

9. The device of claim 1, wherein the plug is coated with silicon varnish.

10. The device of claim 1, wherein the resonance cavity has a volume of 0.1 to 3 $cm^3$.

11. The device according to claim 1, wherein the resonance cavity is outside the plug.

12. The device according to claim 11, wherein the resonance cavity is filled with an acoustically absorbent material.

13. The device according to claim 1, wherein the resonance cavity is inside the plug.

14. The device according to claim 13, wherein the resonance cavity is filled with an acoustically absorbent material.

15. Sound transmission device according to claim 1,
further comprising a supplementary cavity for enclosing a transducer.

16. The device according to claim 15, further comprising a transducer in said supplementary cavity, the transducer being operable as a microphone connected by an electrical cable to a connection device for connecting the transducer to an external transmitter-receiver, the supplementary cavity extending into the residual cavity by a second tube for picking up sound waves of the voice of the user in order to transmit signals representative of said sound waves to such external transmitter-receiver via the connection device.

17. The device of claim 16, further comprising acoustically absorbent material located within the resonance cavity.

18. The device of claim 16, wherein the acoustic valve comprises two resonance cavities, one of the resonance cavities being located outside the plug.

19. The device of claim 18, further comprising acoustically absorbent material located within both resonating cavities.

20. The device of claim 16, wherein said transducer in said supplementary cavity is further operable as a receiver for receiving signals from said external transmitter-receiver via said connection device, transducing said signals, and transmitting sound into said residual cavity via said second tube.

21. The device of claim 16, further comprising a receiver in the acoustic valve and connected to said connection device for receiving signals from such external transmitter-receiver via said connection device, transducing said signals and transmitting sound into said residual cavity via said first tube.

22. A sound transmission device insertable in an outer auditory canal of an individual, comprising:

a plug having an aperture extending longitudinally therethrough, the aperture containing a tube which acoustically couples a residual cavity in the auditory canal formed by the space between the device and an eardrum of the individual with an acoustic valve, the acoustic valve containing at least one resonance cavity, said sound transmission device further comprising:

a microphone located within the plug, a second tube for acoustically connecting the microphone to the residual cavity, a receiver, and a device for electrically connecting an external transmitter-receiver to the receiver and to the microphone, wherein the microphone picks up sound waves created by the individual and transmits signals representative of the sound waves to the external transmitter-receiver.

23. The device of claim 22, further comprising acoustically absorbent material located within the resonance cavity.

24. The device of claim 22, wherein the acoustic valve comprises two resonance cavities, one of the resonance cavities being located outside the plug.

25. The device of claim 24, further comprising acoustically absorbent material located within both resonating cavities.

26. The device of claim 22, wherein said residual cavity and said acoustic valve are acoustically coupled to form a fourth-order acoustic filter with an attenuation slope of at least 30 dB/octave.

27. A sound transmission device insertable in an outer auditory canal of an individual, comprising:

a plug having an aperture extending longitudinally therethrough, the aperture containing a tube which acoustically couples a residual cavity in the auditory canal formed by the space between the device and an eardrum of the individual with an acoustic valve, the acoustic valve containing at least one resonance cavity, said sound transmission device further comprising:

a transducer located within the plug, the transducer being both a microphone and a receiver, a second tube for acoustically connecting the transducer to the residual cavity, and a device for electrically connecting an external transmitter-receiver to the transducer.

28. The device of claim 27, further comprising acoustically absorbent material located within the resonance cavity.

29. The device of claim 27, wherein the acoustic valve comprises two resonance cavities, one of the resonance cavities being located outside the plug.

30. The device of claim 29, further comprising acoustically absorbent material located within both resonating cavities.

31. The device of claim 27, wherein said residual cavity and said acoustic valve are acoustically coupled to form a fourth-order acoustic filter with an attenuation slope of at least 30 dB/octave.

32. The device of claim 1, wherein said fourth-order acoustic filter has an attenuation slope of at least 30 dB/octave.

33. Sound transmission device with selective filtration for being placed in the external auditory canal of a user, including a plug provided with a hole and an acoustic valve at least partially within said plug, said plug being fittable in the auditory canal of the user, the device comprising a tube which opens at its inner end into the residual cavity existing between the plug and the eardrum, and opening at its outer end into the acoustic valve, the acoustic valve defining at least one resonance cavity, wherein said residual cavity and said acoustic valve are acoustically coupled by said tube so as to form an acoustic filter with an attenuation slope of at least 30 dB/octave.

* * * * *